(12) United States Patent
Soula et al.

(10) Patent No.: US 8,669,227 B2
(45) Date of Patent: Mar. 11, 2014

(54) FAST-ACTING INSULIN FORMULATION

(75) Inventors: Olivier Soula, Meyzieu (FR); Remi Soula, Lyons (FR); Gerard Soula, Meyzieu (FR)

(73) Assignee: Adocia, Lyons (FR)

(*) Notice: Subject to any disclaimer, the term of this patent is extended or adjusted under 35 U.S.C. 154(b) by 253 days.

(21) Appl. No.: 12/662,036

(22) Filed: Mar. 29, 2010

(65) Prior Publication Data

US 2010/0249020 A1 Sep. 30, 2010

Related U.S. Application Data

(60) Provisional application No. 61/202,692, filed on Mar. 27, 2009.

(30) Foreign Application Priority Data

Mar. 27, 2009 (FR) ...................................... 09 01478

(51) Int. Cl.
| | | |
|---|---|---|
| A61K 38/28 | (2006.01) | |
| C07K 14/62 | (2006.01) | |
| A61P 3/10 | (2006.01) | |

(52) U.S. Cl.
USPC ............................... 514/5.9; 530/303; 514/54

(58) Field of Classification Search
None
See application file for complete search history.

(56) References Cited

U.S. PATENT DOCUMENTS

| | | | |
|---|---|---|---|
| 2,847,385 A | 8/1958 | Hiler | |
| 4,006,059 A * | 2/1977 | Butler ............................ | 435/176 |
| 4,472,385 A | 9/1984 | Brange et al. | |
| 4,826,818 A | 5/1989 | Mori et al. | |
| 5,929,027 A | 7/1999 | Takama et al. | |
| 8,241,620 B2 | 8/2012 | Dahri-Correia et al. | |
| 2004/0131583 A1* | 7/2004 | Barritault et al. ........... | 424/78.27 |
| 2004/0234616 A1* | 11/2004 | Sabetsky ....................... | 424/493 |
| 2007/0191757 A1 | 8/2007 | Steiner et al. | |
| 2007/0235365 A1 | 10/2007 | Pohl et al. | |
| 2008/0014250 A1 | 1/2008 | Soula et al. | |
| 2008/0039365 A1 | 2/2008 | Steiner et al. | |
| 2008/0039368 A1 | 2/2008 | Steiner et al. | |
| 2008/0096800 A1 | 4/2008 | Pohl et al. | |
| 2008/0234227 A1 | 9/2008 | Soula et al. | |
| 2009/0221805 A1 | 9/2009 | Dahri-Correia et al. | |
| 2009/0291114 A1 | 11/2009 | Soula et al. | |
| 2010/0166867 A1 | 7/2010 | Soula et al. | |
| 2010/0167991 A1 | 7/2010 | Soula et al. | |
| 2010/0227795 A1 | 9/2010 | Steiner et al. | |
| 2011/0159068 A1 | 6/2011 | Soula et al. | |
| 2011/0212901 A1 | 9/2011 | Akiyoshi et al. | |
| 2012/0041079 A1 | 2/2012 | Soula et al. | |
| 2012/0094902 A1 | 4/2012 | Soula et al. | |
| 2012/0295833 A1 | 11/2012 | Charvet | |
| 2012/0309680 A1 | 12/2012 | Charvet | |

FOREIGN PATENT DOCUMENTS

| | | |
|---|---|---|
| EP | 0 214 826 A2 | 3/1987 |
| EP | 0 441 563 A2 | 8/1991 |
| EP | 0 648 495 A2 | 4/1995 |
| EP | 0 681 833 A2 | 11/1995 |
| EP | 0 700 683 A1 | 3/1996 |
| EP | 1 623 979 A1 | 2/2006 |
| FR | 2 224 164 | 10/1974 |
| FR | 2 936 800 A1 | 4/2010 |
| WO | WO 88/06599 A1 | 9/1988 |
| WO | WO 91/09617 A1 | 7/1991 |
| WO | WO 97/49386 A1 | 12/1997 |
| WO | WO 99/34821 A1 | 7/1999 |
| WO | WO 02/053190 A2 | 7/2002 |
| WO | WO 03/00202 A2 | 1/2003 |
| WO | WO 2004/093833 A2 | 11/2004 |
| WO | WO 2005/072803 A1 | 8/2005 |
| WO | WO 2005/089722 A1 | 9/2005 |
| WO | WO 2007/038773 A1 | 4/2007 |
| WO | WO 2007/041481 A1 | 4/2007 |
| WO | WO 2007/116143 A1 | 10/2007 |
| WO | WO 2007/121256 A2 | 10/2007 |
| WO | WO 2008/038111 A1 | 4/2008 |
| WO | WO 2008/084237 A2 | 7/2008 |
| WO | WO 2008/124522 A2 | 10/2008 |
| WO | WO 2008/152106 A1 | 12/2008 |
| WO | WO 2009/048945 A1 | 4/2009 |
| WO | WO 2009/048959 A1 | 4/2009 |
| WO | WO 2009/127940 A1 | 10/2009 |
| WO | WO 2010/028055 A1 | 3/2010 |
| WO | WO 2010/041138 A2 | 4/2010 |
| WO | WO 2010/053140 A1 | 5/2010 |
| WO | WO 2010/058106 A1 | 5/2010 |

(Continued)

OTHER PUBLICATIONS

Demitras et al, Inorganic Chemistry, Prentice-Hall International. Inc., 1972, enclosed pp. 1-5.*
Definition of Phenylalanine, from Croatian English Chemistry Dictionary & Glossary (http://glossary.periodni.com/glossary.php?en=phenylalanine, enclosed, pp. 1-2, Accessed Jan. 17, 2013.*
Janowski et al,Two polymorphs of a covalent complex between papain and a diazomethylketone inhibitor, J. Peptide Res, 2004, 64, pp. 141-150.*
Written Opinion of the International Searching Authority issued in International Application No. PCT/1132010/000711 dated Aug. 7, 2012.
Baudys et al., "Extending Insulin Action in Vivo by Conjugation to Carboxymethyl Dextran," *Bioconjugate Chem.*, vol. 9, No. 2, 1998, pp. 176-183.

(Continued)

*Primary Examiner* — Julie Ha
*Assistant Examiner* — Li Ni Komatsu
(74) *Attorney, Agent, or Firm* — Oliff PLC

(57) ABSTRACT

The invention relates to a complex between an insulin and a polysaccharide comprising carboxyl functional groups, said polysaccharide being chosen from polysaccharides functionalized with at least one phenylalanine derivative, noted Phe, said phenylalanine derivative being chosen from the group consisting of phenylalanine and its alkali metal cation salts, phenylalaninol, phenylalaninamide and ethylbenzylamine or from phenylalanine esters, and said insulin being either a human insulin or an insulin analog. The invention also relates to a pharmaceutical composition comprising at least one complex according to the invention, especially in the form of an injectable solution.

21 Claims, 5 Drawing Sheets

(56) References Cited

FOREIGN PATENT DOCUMENTS

| WO | WO 2010/102020 A1 | 9/2010 |
|----|----|----|
| WO | WO 2010/122385 A1 | 10/2010 |
| WO | WO 2010/149772 A1 | 12/2010 |
| WO | WO 2011/098962 A2 | 8/2011 |

OTHER PUBLICATIONS

Brange et al., "Insulin analogs with improved pharmacokinetic profiles," *Advanced Drug Delivery Reviews*, vol. 35, 1999, pp. 307-335.
Giger et al., "Suppression of Insulin Aggregation by Heparin," *Biomacromolecules*, vol. 9, 2008, pp. 2338-2344.
French Search Report issued in Application No. 09 01478; Issued on Oct. 14, 2009 (With Translation).
Arranz et al., "Water-insoluble dextrans by grafting, 3a) Reaction of dextran with butyl isocyanate. Chemical hydrolysis," Makromol. Chem., vol. 188, pp. 2831-2838, 1987.
Carpino et al., "Efficiency in Peptide Coupling: 1-Hydroxy-7-azabenzotriazole vs 3,4-Dihydro-3-hydroxy-4-oxo-1,2,3-benzotriazine," *Journal of Organic Chemistry*, vol. 60, pp. 3561-3564, 1995.
Caulfield et al., "The Permeability of Glomerular Capillaries to Graded Dextrans," *The Journal of Cell Biology*, vol. 63, pp. 883-903, 1974.
Chang et al., "Permselectivity of the glomerular capillary wall: III. Restricted transport of polyanions," *Kidney International*, vol. 8, pp. 212-218, 1975.
Engelmann et al., "Preparation of Starch Carbamates in Homogeneous Phase using Different Mixing Conditions," *Starch/Stärke*, 2001, pp. 560-569, vol. 53, Wiley-VCH Verlag GmbH.
Larsen, "Dextran prodrugs—structure and stability in relation to therapeutic activity," *Advanced Drug Delivery Reviews*, 1989, pp. 103-154, vol. 3, Elsevier.

Lou, Xianwen et al., "Simulation of size exclusion chromatography for characterization of supramolecular complex: a theoretical study," *Journal of Chromatography A*, 2004, vol. 1029, pp. 67-75.
Ouari et al., "Synthesis of a Glycolipidic Amphiphilic Nitrone as a New Spin Trap," J. Org. Chem., 1999, pp. 3554-3556, vol. 64, American Chemical Society (with 10 pages of supporting information).
Shen et al., "Synthesis and Characterization of Cellulose Carbamates Having α-Amino Acid Moieties," *Polymer Bulletin*, 2005, pp. 317-322, vol. 55.
Tschantz, William R. et al., "Substrate Binding Is Required for Release of Product from Mammalian Protein Farnesyltransferase," *The Journal of Biological Chemistry*, 1997, vol. 272, No. 15, pp. 9989-9993.
Tsai et al., "Synthesis of Amino Acid Ester Isocyanates: Methyl (S)-2-Isocyanato-3-Phenylpropanoate [Benzenepropanoic acid, α-isocyanato-, methyl ester, (S)]," *Organic Syntheses Coll.*, vol. 10, p. 544, 2004; vol. 78, p. 220, 2002.
Won, "Synthesis of heterobifunctional poly(ethylene glycol) containing an acryloyl group at one end and an isocyanate group at the other end," *Polymer Bulletin*, 2004, pp. 109-115, vol. 52.
Dec. 12, 2011 French Search Report issued in French Patent Application No. 1154039 (with translation).
May 3, 2012 French Search Report issued in French Patent Application No. 1158885 (with translation).
Jul. 12, 2010 International Search Report issued in International Patent Application No. PCT/IB2010/000711 (with translation).
Feb. 28, 2013 Office Action issued in U.S. Appl. No. 13/468,799.
Apr. 2, 2013 International Search Report issued in PCT/FR2012/052543.
U.S. Appl. No. 13/468,799 to Charvet et al., filed May 10, 2012.
U.S. Appl. No. 13/468,849 to Charvet et al., filed Jul. 11, 2012.
U.S. Appl. No. 13/668,000 to Soula et al., filed Nov. 2, 2012.

\* cited by examiner

FAST-ACTING INSULIN FORMULATION

BACKGROUND

The present invention relates to a fast-acting formulation of human recombinant insulin.

Since the production of insulin by genetic engineering, at the start of the 1980s, diabetic patients have benefited from human insulin for their treatment. This product has greatly improved this therapy since the immunological risks associated with the use of non-human insulin, in particular porcine insulin, are eliminated.

One of the problems to be solved for improving the health of diabetic patients is to provide them with insulin formulations that provide a hypoglycemic response similar in terms of kinetics to the physiological response generated by the start of a meal, to enable them to not anticipate the start of their meal time and to perform an insulin injection at the start of the meal.

It is nowadays accepted that the provision of such formulations is essential for the best possible management of the disease.

Genetic engineering has provided a response with the development of rapid insulin analogs. These insulins are modified on one or two amino acids so as to be more rapidly distributed in the blood compartment after subcutaneous injection. These insulins Lispro (Lilly), Novolog (Novo) and Apidra (Aventis) are stable insulin solutions with a hypoglycemic response similar in terms of kinetics to the physiological response generated by the start of a meal. Consequently, patients treated with these rapid insulin analogs no longer have to anticipate their meal time, but can perform the insulin injection at the start of the meal.

The principle of rapid insulin analogs is to form hexamers at a concentration of 100 IU/mL to ensure the stability of the insulin in the commercial product, while at the same time promoting very fast dissociation of these hexamers into monomers after injection so as to obtain a rapid action.

Human insulin as formulated in its commercial form does not make it possible to obtain a hypoglycemic response that is close in terms of kinetics to the physiological response generated by the start of a meal, since, at the concentration of use (100 IU/mL), in the presence of zinc and other excipients such as phenol or cresol, it assembles in the form of a hexamer, whereas it is active in monomer and dimer form. Human insulin is prepared in the form of hexamers to be stable for up to 2 years at 4° C., since, in the form of monomers, it has a very high propensity to aggregate and then to fibrillate, which makes it lose its activity. Furthermore, in this aggregated form, it presents an immunological risk to the patient.

Dissociation of the hexamers into dimers and of the dimers into monomers delays its action by nearly 20 minutes when compared with a rapid insulin analog (Brange J., et al., Advanced Drug Delivery Review, 35, 1999, 307-335).

The drawback of rapid insulin analogs is the modification of the primary structure of human insulin. This modification leads to variations of interaction with the insulin receptors present on a very large number of cell lines, since it is known that the role of the insulin in the body is not limited to its hypoglycemiant activity. Although numerous studies have been performed in this field, it cannot be determined at the present time whether these insulin analogs all have the physiological properties of human insulin.

Furthermore, the kinetics of passage of insulin analogs into the blood, and their kinetics of glycemia reduction, are not optimal and there is a real need for a formulation that has an even shorter action time so as to approach the kinetics of healthy patients.

The company Biodel proposed a solution to this problem, with a human insulin formulation comprising EDTA and citric acid, as described in patent application US 2008/39365. EDTA, via its capacity to complex zinc atoms, and citric acid, via its interactions with the cationic parts, are described as destabilizing the hexameric form of insulin and thus reducing its action time.

However, such a formulation has several drawbacks.

Firstly, the injection of a solution containing citric acid may cause pain at the site of injection, which was indeed reported during various clinical studies performed by Biodel, Business Wire (Sep. 8, 2008).

Moreover, the use of a chelating agent such as EDTA, which is not specific for the zinc atom, may lead to side effects.

Since the use of fast-acting insulin is performed three times a day for type I and type II diabetics, the pain associated with the administration of the product is unacceptable to the patients, and the risks of possible side effects due to the excipients must be avoided at all costs.

SUMMARY

There is thus a real and unsatisfied need for formulations that can significantly reduce the onset of action of injected insulin, whether it is human insulin or an analog.

The present invention makes it possible to solve the various problems outlined above, since it makes it possible especially to produce a human insulin formulation at a pH of between 6.0 and 7.8 and preferably between 6.5 and 7.5 as a solution at 100 IU/mL, said formulation making it possible, after administration, to accelerate the passage of insulin into the blood and/or the reduction of glycemia relative to commercial human insulin products.

The present invention also makes it possible to significantly reduce the onset of action of a fast-acting insulin analog formulation.

The invention consists in forming a complex of insulin with a polysaccharide comprising partially substituted carboxyl functional groups.

The formation of this complex may furthermore be performed by simple mixing of an aqueous insulin solution and an aqueous polysaccharide solution.

The invention also relates to the complex between an insulin and a polysaccharide comprising partially substituted carboxyl functional groups.

DETAILED DESCRIPTION

Figure 1:
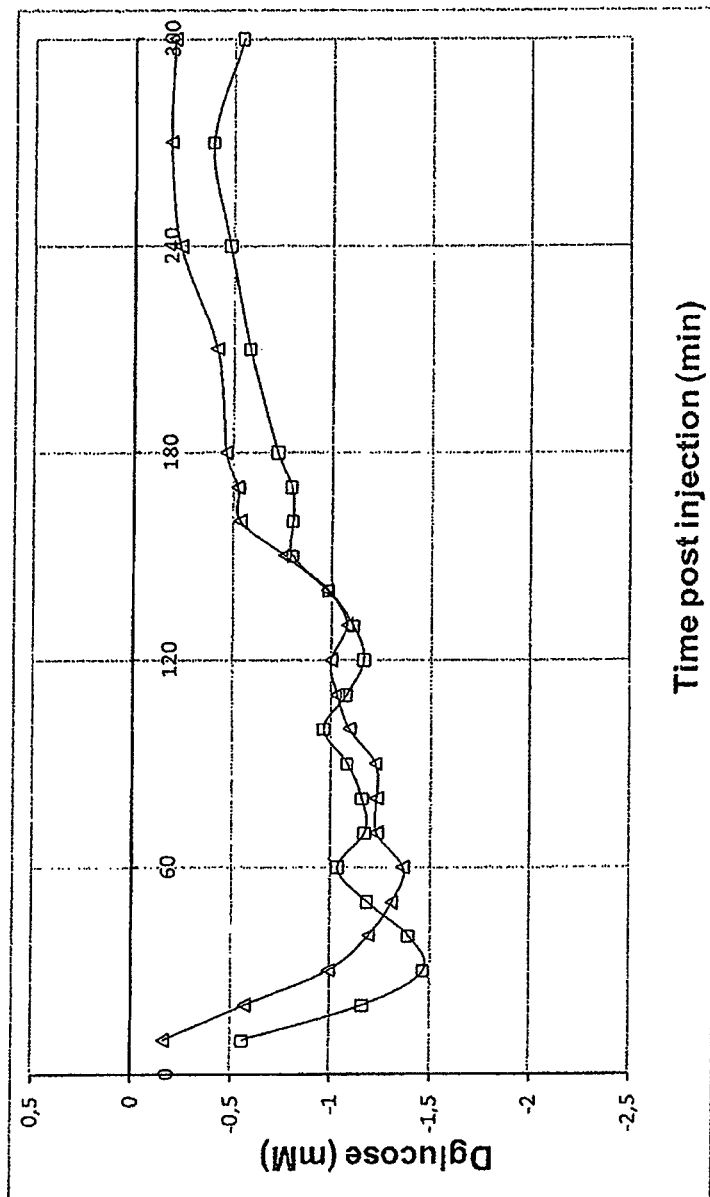
FIG. 1 shows the results obtained with the human insulin formulation described in Example 5. The curves show that the formulation of complex between polymer 1 and human insulin according to the present application (curve plotted with the squares corresponding to Example 5) makes it possible to obtain an onset of action lower than that of a commercial human insulin formulation (curve plotted with the triangles corresponding to Example 2).

In one embodiment, the insulin is human insulin.

The term "human insulin" means an insulin obtained by synthesis or recombination, in which the peptide sequence is the sequence of human insulin, including the allelic variations and the homologs.

In one embodiment, the invention relates to the complex between human insulin and a polysaccharide comprising partially substituted carboxyl functional groups.

The invention also relates to the use of this complex for preparing human insulin formulations, which makes it possible, after administration, to accelerate the passage of insulin into the blood and/or the reduction of glycemia relative to commercial human insulin products.

"Regular" human insulin formulations on the market at a concentration of 600 µM (100 IU/mL) have an onset of action of between 30 and 60 minutes and a glycemic nadir of between 2 and 4 hours.

The fast-acting insulin analog formulations on the market at a concentration of 600 µM (100 IU/mL) have an onset of action of between 10 and 15 minutes and a glycemic nadir of between 60 and 90 minutes.

The invention more particularly relates to the use of a complex according to the invention for the preparation of a "fast-acting" human insulin formulation.

The invention relates to the use of the complex according to the invention for preparing human insulin formulations at a concentration in the region of 600 µM (100 IU/mL), whose onset of action is less than 30 minutes, preferably less than 20 minutes and even more preferably less than 15 minutes.

The invention relates to the use of the complex according to the invention for preparing human insulin formulations at a concentration in the region of 600 µM (100 IU/mL), whose glycemic nadir is less than 120 minutes, preferably less than 105 minutes and more preferably less than 90 minutes.

In one embodiment, the insulin is an insulin analog. The term "insulin analog" means a recombinant insulin whose primary sequence contains at least one modification relative to the primary sequence of human insulin.

In one embodiment, the insulin analog is chosen from the group consisting of the insulin Lispro (Humalog®), the insulin Aspart (Novolog®, Novorapid®) and the insulin glulisine (Apidra®).

In one embodiment, the invention relates to the complex between an insulin analog and a polysaccharide comprising carboxyl functional groups.

In one embodiment, the invention relates to the complex between an insulin analog chosen from the group consisting of the insulin Lispro (Humalog®), the insulin Aspart (Novolog®, Novorapid®) and the insulin glulisine (Apidra®) and a polysaccharide comprising carboxyl functional groups.

The invention also relates to the use of this complex for preparing insulin analog formulations that make it possible to reach, after administration, a plasmatic level of insulin and/or a reduction of glucose more quickly than insulin analog formulations.

The fast-acting insulin analog formulations available on the market at a concentration of 600 µM (100 IU/mL) have an onset of action of between 10 and 15 minutes and a glycemic nadir of between 60 and 90 minutes.

The invention more particularly relates to the use of a complex according to the invention for the preparation of a fast-acting insulin analog formulation.

The invention relates to the use of the complex according to the invention for preparing insulin analog formulations at a concentration in the region of 600 µM (100 IU/mL), whose onset of action is less than 15 minutes and preferably less than 10 minutes.

The invention relates to the use of the complex according to the invention for preparing insulin analog formulations at a concentration in the region of 600 µM (100 IU/mL), whose glycemic nadir is less than 90 minutes and preferably less than 80 minutes.

In one embodiment, the polysaccharide comprising carboxyl functional groups is chosen from functionalized polysaccharides predominantly consisting of glycoside bonds of (1,6) type and, in one embodiment, the polysaccharide predominantly consisting of glycoside bonds of (1,6) type is a functionalized dextran comprising carboxyl functional groups.

Said polysaccharides are functionalized with at least one phenylalanine derivative, noted Phe:

said phenylalanine derivative being grafted or bonded onto the polysaccharides by coupling with an acid function, said acid function being an acid function borne by a linker arm R bonded to the polysaccharide via a function F, said function F resulting from coupling between the linker arm R and an —OH function of the polysaccharide, F being either an ester, thioester, carbonate, carbamate or ether function, R being a chain comprising between 1 and 18 carbons, which is optionally branched and/or unsaturated, comprising one or more heteroatoms, such as O, N and/or S, and having at least one carboxyl function, Phe being a residue of a phenylalanine derivative, L or D, produced from coupling between the phenylalanine amine and at least one acid borne by the group R and/or an acid borne by the polysaccharide comprising carboxyl functional groups.

According to the invention, the functionalized polysaccharides may correspond to the following general formulae:

Formula I

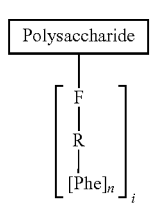

the polysaccharide being a dextran,

F resulting from coupling between the linker arm R and an —OH function of the polysaccharide and being either an ester, thioester, carbonate, carbamate or ether function, R being a chain comprising between 1 and 18 carbons, which is optionally branched and/or unsaturated, comprising one or more heteroatoms, such as O, N and/or S, and having at least one carboxyl function, Phe being a residue of a phenylalanine derivative, L or D, produced from coupling between the amine of the phenylalanine derivative and at least one acid borne by the group R and/or an acid borne by the polysaccharide comprising carboxyl functional groups, n represents the mole fraction of R substituted with Phe and is between 0.3 and 0.9, preferably between 0.4 and 0.8 and more preferably between 0.4 and 0.6, i represents the average mole fraction of groups F—R—[Phe]$_n$ borne per saccharide unit and is between 0.5 and 2.5, preferably between 0.8 and 1.6, preferably between 1.0 and 1.4 and preferably between 1.0 and 1.2;

when R is not substituted with Phe, then the acid(s) of the group R are carboxylates of a cation, preferably an alkali metal cation such as Na$^+$ or K$^+$.

In one embodiment, n, which represents the mole fraction of R substituted with Phe, is between 0.3 and 0.9, preferably between 0.4 and 0.8 and more preferably between 0.4 and 0.6.

The polysaccharide comprises on average at least 60 substituted or unsubstituted carboxylate units per 100 saccharide units.

In one embodiment, F is either an ester, a carbonate, a carbamate or an ether.

In one embodiment, the polysaccharide according to the invention is characterized in that the group R is chosen from the following groups:

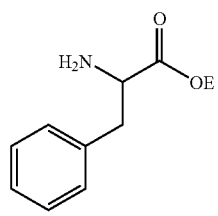

or the alkali metal cation salts thereof.

In one embodiment, the polysaccharide according to the invention is characterized in that the phenylalanine derivative is chosen from the group consisting of phenylalanine and alkali metal cation salts thereof, phenylalaninol, phenylalaninamide and ethylbenzylamine.

In one embodiment, the polysaccharide according to the invention is characterized in that the phenylalanine derivative is chosen from the phenylalanine esters of formula II Formula II E being a linear or branched C1 to C6 alkyl group.

The polysaccharide may have a degree of polymerization of between 10 and 3000.

In one embodiment, it has a degree of polymerization of between 10 and 400.

In another embodiment, it has a degree of polymerization of between 10 and 200.

In another embodiment, it has a degree of polymerization of between 30 and 50.

In one embodiment, the polysaccharide has a mass of between 9 and 50 kD and preferably between 10 and 40 kD.

In one embodiment, the insulin is a human recombinant insulin as described in the European Pharmacopea.

In one embodiment, the insulin is an insulin analog chosen from the group consisting of the insulin Lispro (Humalog®), the insulin Aspart (Novolog®, Novorapid®) and the insulin glulisine (Apidra®).

In one embodiment, the polymer/insulin mole ratios are between 0.2 and 5.

In one embodiment, they are between 0.2 and 3.

In one embodiment, they are between 0.6 and 2.5.

In one embodiment, they are between 0.8 and 2.

In one embodiment, they are between 0.8 and 1.4.

In one embodiment, the mole ratio is equal to 1.

In one embodiment, the mole ratio is equal to 2.

In one embodiment, the polymer/insulin mass ratios are between 0.4 and 10.

In one embodiment, they are between 0.4 and 6.

In one embodiment, they are between 1.2 and 5.

In one embodiment, they are between 1.6 and 4.

In one embodiment, they are between 1.6 and 2.8.

Preferably, this composition is in the form of an injectable solution.

In one embodiment, the insulin concentration of the solutions is 600 μM, i.e. 100 IU/mL.

In one embodiment, the insulin concentration of 600 μM may be reduced by simple dilution, in particular for pediatric applications.

The invention also relates to a pharmaceutical composition according to the invention, characterized in that it is obtained by drying and/or lyophilization.

In the case of local and systemic releases, the envisioned administration modes are intravenous, subcutaneous, intradermal or intramuscular.

The transdermal, oral, nasal, vaginal, ocular, buccal and pulmonary administration routes are also envisioned.

The invention also relates to the use of a complex according to the invention for the formulation of a solution of human insulin with a concentration of 100 IU/mL intended for implantable or transportable insulin pumps.

Example 1

Fast-Acting Insulin Analog Solution at 100 IU/mL

This solution is a commercial solution of Aspart insulin sold by the company Novo under the name Novolog® in the USA and Novorapid® in Europe. This product is a fast-acting insulin analog.

Example 2

Solution of Human Insulin at 100 IU/mL

This solution is a commercial solution from Novo sold under the name Actrapid. This product is a human insulin.

Example 3

Preparation of a Solution of Human Insulin at 200 IU/mL 60.4 g of water are added to 884.7 mg of human insulin comprising two $Zn^{2+}$ per hexamer, and the pH is then adjusted from 5.7 to 3 by adding 8 mL of 0.1 N HCl. The solution is neutralized to pH 7 by adding 10 mL of 0.1 N NaOH. The concentration is then adjusted to 200 IU/mL with 43.08 mL of water. The final pH of this solution is 7.02. The solution is finally filtered through a 0.22 µm membrane.

Example 4

Preparation of the Excipients

Preparation of the 200 mM pH 7 Phosphate Buffer

A solution A of monosodium phosphate is prepared as follows: 1.2 g of $NaH_2PO_4$ (10 mmol) are solubilized in 50 mL of water in a graduated flask.

A solution B of disodium phosphate is prepared as follows: 1.42 g of $Na_2HPO_4$ (10 mmol) are solubilized in 50 mL of water in a graduated flask.

The 200 mM pH 7 phosphate buffer is obtained by mixing 3 mL of solution A with 7 mL of solution B.

Preparation of a 130 mM m-Cresol Solution

The m-cresol solution is obtained by solubilizing 0.281 g of m-cresol (2.6 mmol) in 20 mL of water in a graduated flask.

Preparation of a 0.8 mM Tween 20 Solution

The Tween 20 solution is obtained by solubilizing 98 mg of Tween 20 (80 µmol) in 100 mL of water in a graduated flask.

Preparation of a 1.5 M Glycerol Solution

The glycerol solution is obtained by solubilizing 13.82 g of glycerol (150 mmol) in 100 mL of water in a graduated flask.

Preparation of the Polysaccharide Solutions

Two polysaccharides according to the invention are used.

Polymer 1 is a sodium dextran methylcarboxylate modified with the sodium salt of L-phenylalanine obtained from a dextran with a weight-average molar mass of 10 kg/mol, i.e. a degree of polymerization of 39 (Pharmacosmos) according to the process described in patent application FR 07/02316. The average mole fraction of sodium methylcarboxylates, optionally modified with phenylalanine, i.e. i in formula I, is 1.06. The average mole fraction of sodium methylcarboxylates modified with phenylalanine, i.e. n in formula I, is 0.43.

The solution of polymer 1 is obtained by solubilizing 2.79 g of polymer 1 (water content=10%) in 25.3 mL of water in a 50 mL tube (concentration of polymer 1 of 99.2 mg/mL).

Polymer 2 is a sodium dextran methylcarboxylate modified with the ethyl ester of L-phenylalanine obtained from a dextran with a weight-average molar mass of 40 kg/mol, i.e. a degree of polymerization of 154 (Pharmacosmos) according to a process similar to that described for polymer 1 in patent application FR 07/02316, using L-phenylalanine ethyl ester hydrochloride. The average mole fraction of sodium methylcarboxylates, optionally modified with phenylalanine, i.e. i in formula I, is 1.00. The average mole fraction of sodium methylcarboxylates modified with L-phenylalanine ethyl ester, i.e. n in formula I, is 0.36.

The solution of polymer 2 is obtained by solubilizing 1.33 g of polymer 2 (water content=10%) in 16.83 mL of water in a 50 mL tube (concentration of polymer 2 of 71.0 mg/mL).

Polymer 3 is a sodium dextran methylcarboxylate modified with the sodium salt of L-phenylalanine obtained from a dextran with a weight-average molar mass of 10 kg/mol, i.e. a degree of polymerization of 39 (Pharmacosmos) according to the process described in patent application FR 07/02316. The average mole fraction of sodium methylcarboxylates, optionally modified with phenylalanine, i.e. i in formula I, is 1.06. The average mole fraction of sodium methylcarboxylates modified with phenylalanine, i.e. n in formula I, is 0.54.

The solution of polymer 3 is obtained by solubilizing 1.5 g of polymer 3 (water content=10%) in 42.7 mL of water in a 50 mL tube (concentration of polymer 3 of 31.6 mg/mL).

Polymer 4 is a sodium dextran methylcarboxylate modified with the sodium salt of L-phenylalanine obtained from a dextran with a weight-average molar mass of 10 kg/mol, i.e. a degree of polymerization of 39 (Pharmacosmos) according to the process described in patent application FR 07/02316. The average mole fraction of sodium methylcarboxylates, optionally modified with phenylalanine, i.e. i in formula I, is 1.69. The average mole fraction of sodium methylcarboxylates modified with phenylalanine, i.e. n in formula I, is 0.64.

The solution of polymer 4 is obtained by solubilizing 2.0 g of polymer 4 (water content=10%) in 56.9 mL of water in a 50 mL tube (concentration of polymer 4 of 31.6 mg/mL).

Example 5

Preparation of a Solution of Human Insulin at 100 IU/mL in the Presence of Polymer 1

For a final volume of 50 mL of formulation with a [polymer 1]/[insulin] mole ratio of 1.0, the various reagents are mixed together in the amounts specified in the table below and in the following order:

| | |
|---|---|
| Human insulin at 200 IU/mL | 25 mL |
| Polymer 1 at 99.2 mg/mL | 3.61 mL |
| pH 7 1 M phosphate buffer | 500 µL |
| 0.78 mM Tween 20 | 516 µL |
| 1.5 M glycerol | 621 µL |
| 130 mM m-cresol | 11.15 mL |
| Water (volume for dilution − volume of sodium hydroxide) | 8.55 mL |

The final pH is 7±0.3.

This clear solution is filtered through a 0.22 µm membrane and is then placed at +4° C.

Example 6

Preparation of a Solution of Human Insulin at 100 IU/mL in the Presence of Polymer 2

For a final volume of 50 mL of formulation with a [polymer 2]/[insulin] mole ratio of 0.5, the various reagents are mixed together in the amounts specified in the table below and in the following order:

| | |
|---|---:|
| Human insulin at 200 IU/mL | 10 mL |
| Polymer 2 at 71.0 mg/mL | 9.66 mL |
| pH 7 1 M phosphate buffer | 500 μL |
| 0.78 mM Tween 20 | 400 μL |
| 1.5 M glycerol | 5.67 μL |
| 130 mM m-cresol | 11.16 mL |
| Water (volume for dilution - volume of sodium hydroxide) | 12.6 mL |

The final pH is 7±0.3.
This clear solution is filtered through a 0.22 μm membrane and is then placed at +4° C.

Example 7

Preparation of a Solution of Human Insulin at 100 IU/mL in the Presence of Polymer 3

For a final volume of 50 mL of formulation with a [polymer 3]/[insulin] mole ratio of 1.0, the various reagents are mixed together in the amounts specified in the table below and in the following order:

| | |
|---|---:|
| Human insulin at 500 IU/mL | 10 mL |
| Polymer 3 at 31.6 mg/mL | 11.9 mL |
| pH 7 1 M phosphate buffer | 500 μL |
| 1.5 M glycerol | 5.67 mL |
| 130 mM m-cresol | 11.16 mL |
| 1 mM Tween 20 | 0.4 mL |
| Water (volume for dilution - volume of sodium hydroxide) | 10.4 mL |

The final pH is 7±0.3.
This clear solution is filtered through a 0.22 μm membrane and is then placed at +4° C.

Example 8

Preparation of a Solution of Insulin Analog at 100 IU/mL in the Presence of Polymer 3

For a final volume of 10 mL of formulation with a [polymer 3]/[insulin analog] mole ratio of 1.0, the various reagents are mixed together in the amounts specified in the table below and in the following order:

| | |
|---|---:|
| Solution of the commercial product Novolog | 10 mL |
| Lyophilized polymer 3 | 376 mg |
| Tween 20 | 98 μg |

The final pH is 7±0.3.
This clear solution is filtered through a 0.22 μm membrane and is then placed at +4° C.

Example 9

Preparation of a Solution of Human Insulin at 100 IU/mL in the Presence of Polymer 1

For a final volume of 50 mL of formulation with a [polymer 1]/[insulin] mole ratio of 2.0, the various reagents are mixed together in the amounts specified in the table below and in the following order:

| | |
|---|---:|
| Human insulin at 200 IU/mL | 25 mL |
| Polymer 1 at 99.2 mg/mL | 7.22 mL |
| pH 7 1 M phosphate buffer | 500 μL |
| 0.78 mM Tween 20 | 516 μL |
| 1.5 M glycerol | 621 μL |
| 130 mM m-cresol | 11.15 mL |
| Water (volume for dilution - volume of sodium hydroxide) | 4.94 mL |

The final pH is 7±0.3.
This clear solution is filtered through a 0.22 μm membrane and is then placed at +4° C.

Example 10

Preparation of a Solution of Human Insulin at 100 IU/mL in the Presence of Polymer 3

A variant of the human insulin formulation with polymer 3 described in Example 7 is prepared in the absence of phosphate. This solution otherwise has the same composition and a pH also of 7±0.3.

Example 11

Preparation of a Solution of Human Insulin at 100 IU/mL in the Presence of Polymer 3

A variant of the human insulin formulation with polymer 3 described in Example 7 is prepared in the absence of phosphate and of Tween. This solution otherwise has the same composition and a pH also of 7±0.3.

Example 12

Preparation of a Solution of Human Insulin at 100 IU/mL in the Presence of Polymer 4

A variant of the human insulin formulation described in Example 7 is prepared using a solution of polymer 4 instead of the solution of polymer 3. This solution otherwise has the same composition and a pH also of 7±0.3.

Example 13

Injectability of the Solutions

All these solutions are injectable with the usual insulin injection systems. The solutions described in Examples 1, 2, 5 and 6 are injected just as easily with insulin syringes with 31-gauge needles as with Novo insulin pens, sold under the name Novopen, equipped with 31-gauge needles.

Example 14

Protocol for Measuring the Pharmacodynamics of the Insulin Solutions 6 domestic pigs weighing about 50 kg, catheterized beforehand in the jugular vein, are fasted for 2 to 3 hours before the start of the experiment. In the hour preceding the injection of insulin, 3 blood samples are taken in order to determine the basal glucose level.

The injection of insulin at a dose of 0.125 IU/kg is performed subcutaneously into the neck, under the animal's ear using a Novopen insulin pen equipped with a 31 G needle.

Blood samples are then taken every 10 minutes over 3 hours and then every 30 minutes up to 5 hours. After taking each sample, the catheter is rinsed with a dilute heparin solution.

A drop of blood is taken to determine the glycemia using a glucometer.

The glucose pharmacodynamics curves are then plotted.

Example 15

Pharmacodynamics Results for the Insulin Solutions

| Example | Insulin | Polymer | Polymer/insulin mole ratio | Number of pigs |
|---|---|---|---|---|
| 1 | Analog | — | — | 24 |
| 2 | Human | — | — | 31 |
| 5 | Human | 1 | 1.0 | 24 |
| 6 | Human | 2 | 0.5 | 21 |
| 7 | Human | 3 | 1.0 | 9 |
| 8 | Analog | 3 | 1.0 | 11 |
| 9 | Human | 1 | 2.0 | 5 |

The results obtained with the human insulin formulation described in Example 5 are represented by the curves in FIG. 1. The curves show that the formulation of complex between polymer 1 and human insulin according to the invention (curve plotted with the squares corresponding to Example 5) makes it possible to obtain an onset of action of less than that of a commercial human insulin formulation (curve plotted with the triangles corresponding to Example 2).

Figure 2:
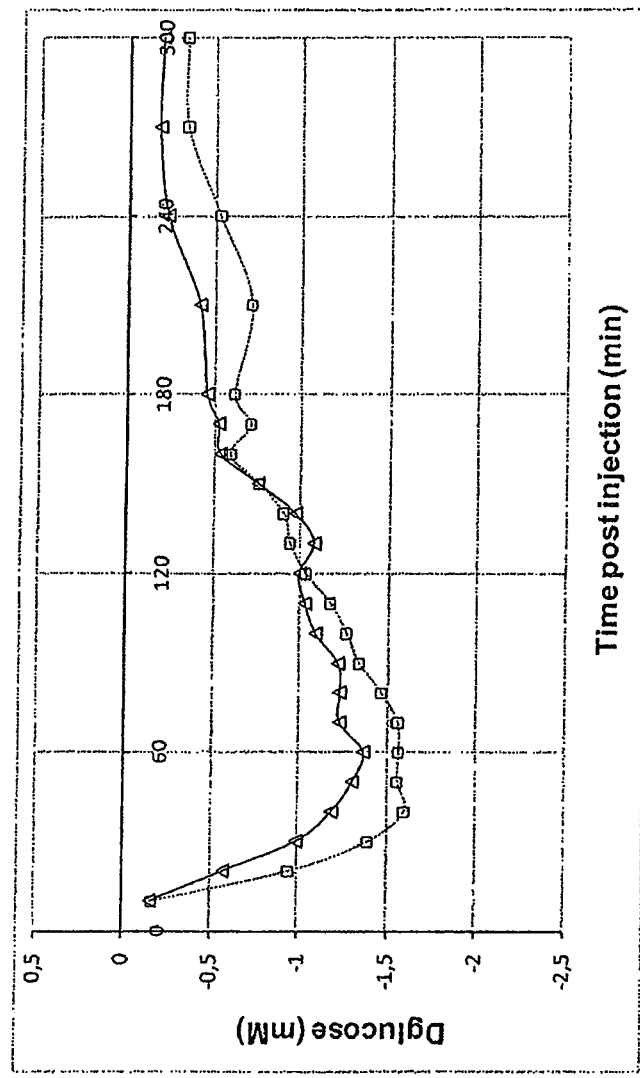
FIG. 2 shows the results obtained with the human insulin formulation described in Example 6. The curves show that the formulation of the complex between polymer 2 and human insulin according to the present application (curve plotted with the squares corresponding to Example 6) makes it possible to obtain an onset of action lower than that of a commercial human insulin formulation (curve plotted with the triangles corresponding to Example 2).

The results obtained with the human insulin formulation described in Example 6 are represented by the curves in FIG. 2. The curves show that the formulation of the complex between polymer 2 and human insulin according to the invention (curve plotted with the squares corresponding to Example 6) make it possible to obtain an onset of action lower than that of a commercial human insulin formulation (curve plotted with the triangles corresponding to Example 2).

Figure 3:
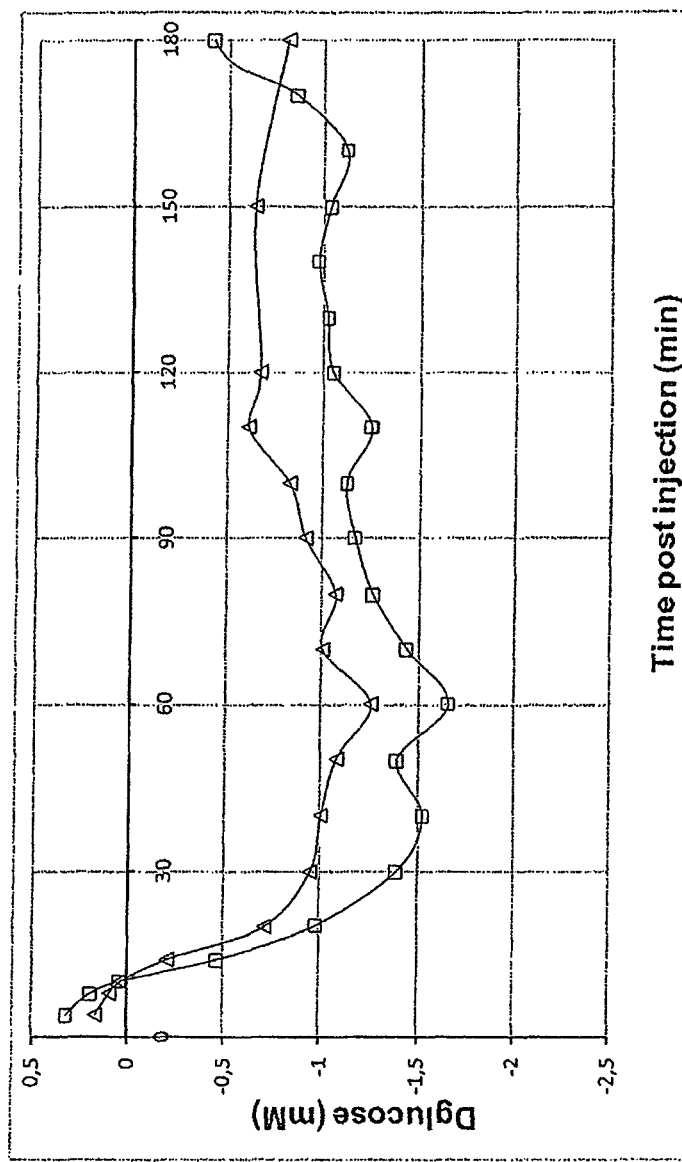
FIG. 3 shows the results obtained with the human insulin formulation described in Example 7. The curves show that the formulation of the complex between polymer 3 and human insulin according to the present application (curve plotted with the squares corresponding to Example 7) makes it possible to obtain an onset of action lower than that of a commercial human insulin formulation (curve plotted with the triangles corresponding to Example 2).

The results obtained with the human insulin formulation described in Example 7 are represented by the curves in FIG. 3. The curves show that the formulation of the complex between polymer 3 and human insulin according to the invention (curve plotted with the squares corresponding to Example 7) make it possible to obtain an onset of action lower than that of a commercial human insulin formulation (curve plotted with the triangles corresponding to Example 2).

Figure 4:
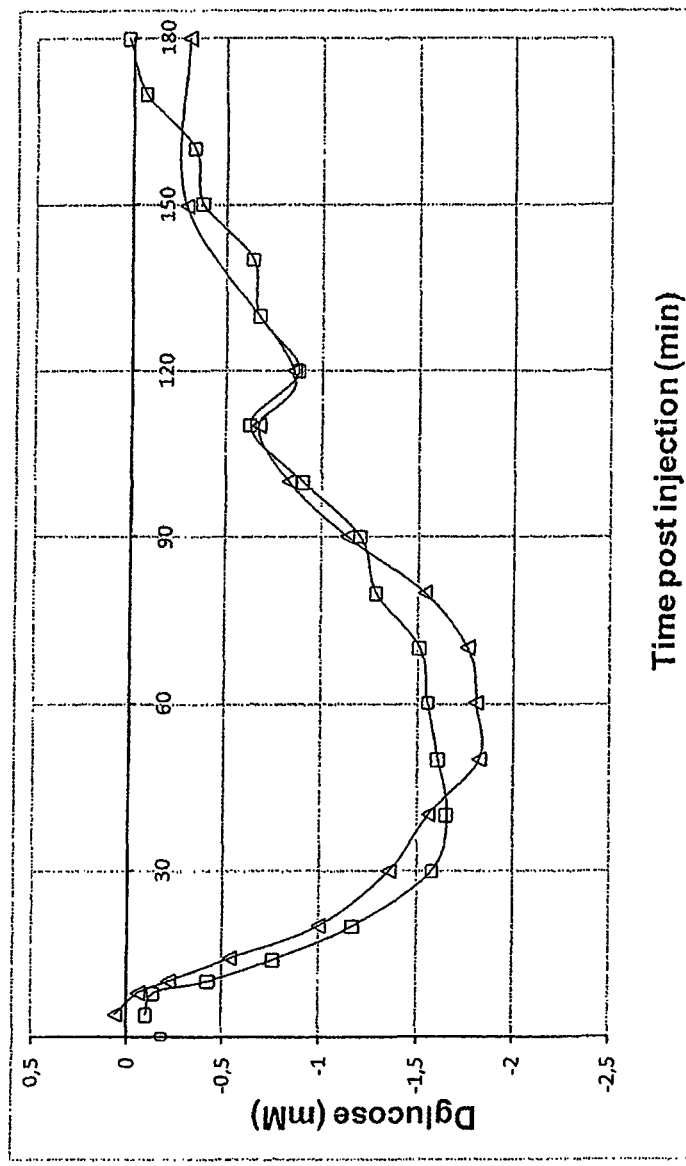
FIG. 4 shows the results obtained with the insulin analog formulation described in Example 8. The curves show that the formulation of the complex between polymer 3 and an insulin analog according to the present application (curve plotted with the squares corresponding to Example 8) makes it possible to obtain an onset of action lower than that of a commercial formulation of this insulin analog (curve plotted with the triangles corresponding to Example 1).

The results obtained with the insulin analog formulation described in Example 8 are represented by the curves in FIG. 4. The curves show that the formulation of the complex between polymer 3 and an insulin analog according to the invention (curve plotted with the squares corresponding to Example 8) make it possible to obtain an onset of action lower than that of a commercial formulation of this insulin analog (curve plotted with the triangles corresponding to Example 1).

Figure 5:
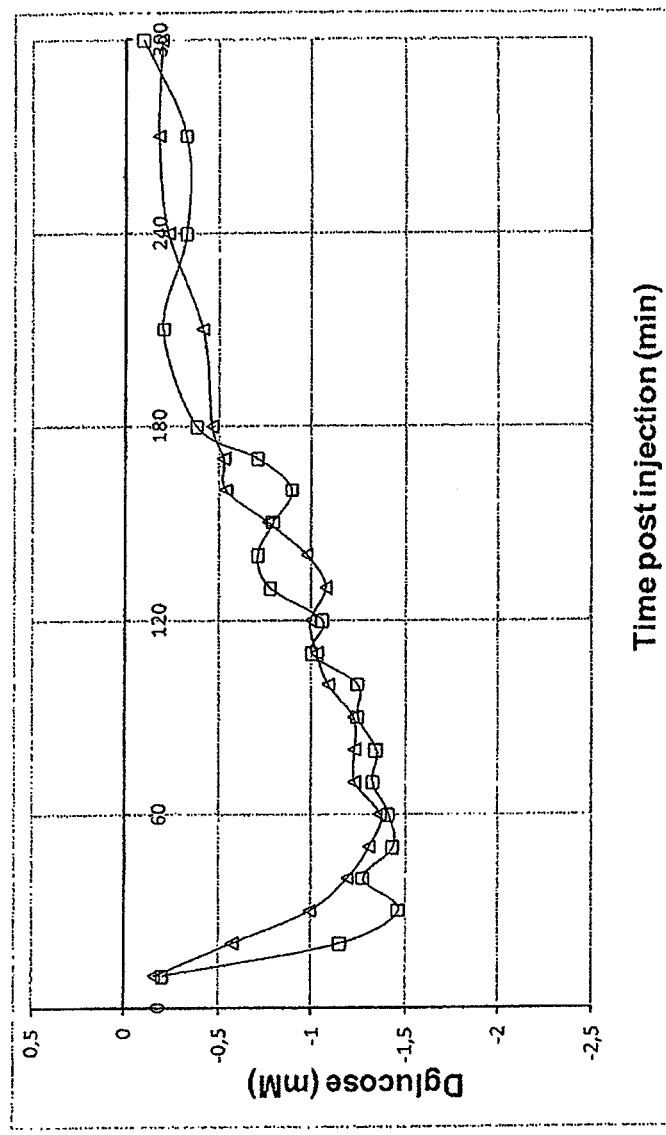
FIG. 5 shows the results obtained with the human insulin formulation described in Example 9. The curves show that the formulation of the complex between polymer 1 and the human insulin according to the present application (curve plotted with the squares corresponding to Example 9) makes it possible to obtain an onset of action lower than that of a commercial human insulin formulation (curve plotted with the triangles corresponding to Example 2).

The results obtained with the human insulin formulation described in Example 9 are represented by the curves in FIG. 5. The curves show that the formulation of the complex between polymer 1 and the human insulin according to the invention (curve plotted with the squares corresponding to Example 9) make it possible to obtain an onset of action lower than that of a commercial human insulin formulation (curve plotted with the triangles corresponding to Example 2).

The invention claimed is:

1. A water soluble non-covalent complex between an insulin and a polysaccharide comprising carboxyl functional groups, wherein said polysaccharide is a polysaccharide functionalized with at least one phenylalanine (abbreviated Phe), said phenylalanine being grafted or bonded onto the polysaccharide by coupling with an acid group, said acid group being borne by a linker arm R bonded to the polysaccharide via a group F, said group F resulting from coupling between the linker arm R and an —OH group of the polysaccharide and/or borne by the polysaccharide comprising carboxyl functional groups, wherein:

F is either an ester, thioester, carbonate, carbamate or ether group;

R is a chain comprising between 1 and 18 carbons, being optionally branched and/or unsaturated, comprising one or more heteroatoms, and having at least one carboxyl group or a salt thereof prior to attachment of Phe, or a chain, not substituted with Phe, comprising between 1 and 18 carbons, being optionally branched and/or unsaturated, comprising one or more heteroatoms, and having at least one carboxyl group or a salt thereof; and Phe is a residue of phenylalanine, L or D enantiomer, or alkali metal cation salts thereof, produced from coupling between the amine of the phenylalanine and at least one acid borne by the group R and/or an acid borne by the polysaccharide comprising carboxyl functional groups.

2. The complex according to claim 1, wherein the polysaccharide is a polysaccharide of formula I;

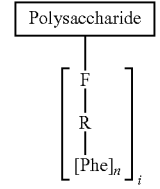

Formula I wherein the polysaccharide is a dextran;

F results from coupling between the linker arm R and an —OH group of the polysaccharide and is either an ester, thioester, carbonate, carbamate or ether group;

R is a chain comprising between 1 and 18 carbons, being optionally branched and/or unsaturated, comprising one or more heteroatoms, and having at least one carboxyl group or a salt thereof prior to attachment of Phe; Phe is a residue of phenylalanine, L or D enantiomer, produced from coupling between the amine of the phenylalanine and at least one acid borne by the group R and/or an acid borne by the polysaccharide comprising carboxyl functional groups, n is a mole fraction of R substituted with Phe and is between 0.3 and 0.9;

i is an average mole fraction of groups F—R-[Phe]$_n$ borne per saccharide unit and is between 0.5 and 2.5; and when R is not substituted with Phe, then the acid(s) of the group R are carboxylates of an alkali metal cation, wherein the alkali metal cation is selected from the group consisting of $K^+$ and $Na^+$.

3. The complex according to claim 1, wherein F is an ester, a carbonate, a carbamate or an ether group.

4. The complex according to claim 1, wherein the group R, prior to attachment of Phe, is selected from the group consisting of:

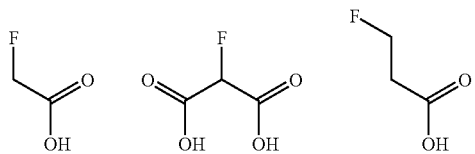 [SMILES: O=C(O)CF ; O=C(O)C(F)C(=O)O ; O=C(O)CCF]

and alkali metal cation salts thereof, wherein the alkali metal cation is selected from the group consisting of $K^+$ and $Na^+$.

5. The complex according to claim 1, wherein the insulin is a human recombinant insulin.

6. The complex according to claim 1, wherein the insulin is an insulin analog.

7. The complex according to claim 6, wherein the insulin analog is selected from the group consisting of insulin lispro, insulin aspart and insulin glulisine.

8. The complex according to claim 1, wherein a polysaccharide/insulin mole ratio is between 0.2 and 5.

9. The complex according to claim 1, wherein a polysaccharide/insulin mole ratio is between 0.2 and 3.

10. The complex according to claim 1, wherein a polysaccharide/insulin mole ratio is equal to 1.

11. The complex according to claim 1, wherein a polysaccharide/insulin mole ratio is equal to 2.

12. The complex according to claim 1, wherein a polysaccharide/insulin mass ratio is between 0.4 and 10.

13. The complex according to claim 1, wherein a polysaccharide/insulin mass ratio is between 0.4 and 6.

14. A pharmaceutical composition comprising at least one complex according to claim 1.

15. The composition according to claim 14, wherein the composition is in a form of an injectable solution.

16. The composition according to claim 15, wherein the insulin concentration of the solution is 600 μmol/mL or 100 IU/mL.

17. A method of preparing a human insulin formulation, comprising:
adding the complex as claimed in claim 1 to a formulation, wherein the human insulin formulation has an insulin concentration of about 600 μM or 100 IU/mL, and an onset of action less than 30 minutes.

18. A method of preparing a human insulin formulation, comprising:
adding the complex as claimed in claim 1 to a formulation, wherein the human insulin formulation has an insulin concentration of about 600 μmol/L or 100 IU/mL, and a glycemic nadir less than 120 minutes.

19. A method of preparing an insulin analog formulation, comprising:
adding the complex as claimed in claim 1 to a formulation, wherein the insulin analog formulation has an insulin concentration of about 600 μM or 100 IU/mL, and an onset of action less than 15 minutes.

20. A method of preparing an insulin analog formulation, comprising:
adding the complex as claimed in claim 1 to a formulation, wherein the insulin analog formulation has an insulin concentration of about 600 μmol/L or 100 IU/mL, and a glycemic nadir less than 90 minutes.

21. A method of preparing an insulin formulation for injection pumps, comprising:
adding the complex as claimed in claim 1 to a formulation, wherein the insulin formulation has an insulin concentration of 100 IU/mL.

\* \* \* \* \*